(12) United States Patent
McClellan et al.

(10) Patent No.: US 9,351,719 B2
(45) Date of Patent: May 31, 2016

(54) SELF LOCKING KNOTLESS SUTURE

(71) Applicant: Zone 2 Surgical, Inc., Morgantown, WV (US)

(72) Inventors: William T. McClellan, Morgantown, WV (US); Scott Heneveld, Whitmore, CA (US); David Skinlo, North Logan, UT (US); Ephraim Akyuz, Logan, UT (US)

(73) Assignee: ZONE 2 SURGICAL, INC., Morgantown, WV (US)

(*) Notice: Subject to any disclaimer, the term of this patent is extended or adjusted under 35 U.S.C. 154(b) by 225 days.

(21) Appl. No.: 14/068,425

(22) Filed: Oct. 31, 2013

(65) Prior Publication Data
US 2014/0128888 A1 May 8, 2014

Related U.S. Application Data

(60) Provisional application No. 61/721,158, filed on Nov. 1, 2012.

(51) Int. Cl.
*A61B 17/04* (2006.01)
*A61B 17/06* (2006.01)

(52) U.S. Cl.
CPC ............ *A61B 17/04* (2013.01); *A61B 17/0483* (2013.01); *A61B 17/0487* (2013.01); *A61B 17/06166* (2013.01); *A61B 17/06* (2013.01); *A61B 2017/06176* (2013.01)

(58) Field of Classification Search
CPC ............... A61B 17/0487; A61B 17/06166; A61B 17/06; A61B 17/06176; A61B 17/04; A61B 17/0483
USPC .......................................................... 606/228
See application file for complete search history.

(56) References Cited

U.S. PATENT DOCUMENTS 3,123,077 A 3/1964 Alcamo
3,176,316 A 4/1965 Bodell
(Continued)

FOREIGN PATENT DOCUMENTS

WO WO2011068533 6/2011
WO WO2013055886 4/2013
WO WO2014138570 9/2014

OTHER PUBLICATIONS

Office Action dated Aug. 26, 2015 in U.S. Appl. No. 14/200,655, 12 pages.
(Continued)

*Primary Examiner* — Jonathan W Miles
*Assistant Examiner* — George J Ulsh
(74) *Attorney, Agent, or Firm* — Andrew D. Wright; Roberts Mlotkowski Safran & Cole, P.C.

(57) ABSTRACT

Self-locking knotless sutures and associated methods are disclosed. A system for securing tissue includes a monofilament and a braid having a fixed end and a capture end. A first end of the monofilament is connected to the fixed end of the braid. A second end of the monofilament opposite the first end is a free end. The capture end of the braid has a first opening and a second opening. The monofilament and braid are structured and arranged for the free end of the monofilament to be inserted into the first opening, passed through a tunnel formed by the braid, and passed out of the second opening, all while moving in a first direction. After insertion of the monofilament into the braid, the braid prevents movement of the monofilament in a second direction opposite the first direction to prevent the monofilament from being pulled out of the braid.

16 Claims, 5 Drawing Sheets

(56) References Cited

U.S. PATENT DOCUMENTS

| | | |
|---|---|---|
| 3,541,591 A | 11/1970 | Hoegerman |
| 3,545,008 A | 12/1970 | Bader, Jr. |
| 3,570,497 A | 3/1971 | Lemole |
| 3,664,345 A | 5/1972 | Dabbs et al. |
| 3,805,300 A | 4/1974 | Tascon-Alonso et al. |
| 3,833,200 A | 9/1974 | McCombs, Jr. |
| 3,952,377 A | 4/1976 | Morell |
| 3,976,079 A | 8/1976 | Samuels et al. |
| 4,149,277 A | 4/1979 | Bokros |
| 4,301,551 A | 11/1981 | Dore et al. |
| 4,469,101 A | 9/1984 | Coleman et al. |
| 4,535,764 A | 8/1985 | Ebert |
| 4,688,561 A | 8/1987 | Reese |
| 4,741,330 A | 5/1988 | Hayhurst |
| 4,750,492 A | 6/1988 | Jacobs |
| 4,950,284 A | 8/1990 | Green et al. |
| 4,950,285 A | 8/1990 | Wilk |
| 4,971,075 A | 11/1990 | Lee |
| 4,979,956 A | 12/1990 | Silvestrini |
| 5,053,047 A | 10/1991 | Yoon |
| 5,061,283 A | 10/1991 | Silvestrini |
| 5,123,913 A | 6/1992 | Wilk et al. |
| 5,207,694 A | 5/1993 | Broome |
| 5,269,783 A | 12/1993 | Sander |
| 5,314,436 A | 5/1994 | Wilk |
| 5,318,566 A | 6/1994 | Miller |
| 5,330,489 A | 7/1994 | Green et al. |
| 5,356,412 A | 10/1994 | Golds et al. |
| 5,356,417 A | 10/1994 | Golds |
| 5,366,461 A | 11/1994 | Blasnik |
| 5,372,146 A | 12/1994 | Branch |
| 5,382,257 A | 1/1995 | Lewis et al. |
| 5,391,173 A | 2/1995 | Wilk |
| 5,403,346 A | 4/1995 | Loeser |
| 5,413,585 A | 5/1995 | Pagedas |
| 5,425,766 A | 6/1995 | Bowald |
| 5,462,542 A | 10/1995 | Alesi |
| 5,476,493 A | 12/1995 | Muff |
| 5,520,691 A | 5/1996 | Branch |
| 5,549,122 A | 8/1996 | Detweilwer |
| 5,591,206 A | 1/1997 | Moufarrege |
| 5,643,295 A | 7/1997 | Yoon |
| 5,665,109 A | 9/1997 | Yoon |
| 5,669,935 A | 9/1997 | Rosenman et al. |
| 5,683,417 A | 11/1997 | Cooper |
| 5,704,372 A | 1/1998 | Moll et al. |
| 5,725,556 A | 3/1998 | Moser et al. |
| 5,735,877 A | 4/1998 | Pagedas |
| 5,741,301 A | 4/1998 | Pagedas |
| 5,766,218 A | 6/1998 | Arnott |
| 5,810,853 A | 9/1998 | Yoon |
| 5,850,674 A | 12/1998 | Jansen |
| 5,860,948 A | 1/1999 | Buscemi |
| 5,972,006 A | 10/1999 | Sciaino |
| 5,980,557 A | 11/1999 | Iserin et al. |
| 5,984,933 A | 11/1999 | Yoon |
| 6,007,576 A | 12/1999 | McClellan |
| 6,014,792 A | 1/2000 | Marelin et al. |
| 6,015,428 A | 1/2000 | Pagedas |
| 6,063,106 A | 5/2000 | Gibson |
| 6,066,160 A | 5/2000 | Colvin et al. |
| 6,080,192 A | 6/2000 | Demopulos et al. |
| 6,083,244 A | 7/2000 | Lubbers et al. |
| 6,102,947 A | 8/2000 | Gordon |
| 6,152,895 A | 11/2000 | Wilk |
| 6,200,318 B1 | 3/2001 | Har-Shai et al. |
| 6,432,123 B2 | 8/2002 | Schwartz et al. |
| 6,485,504 B1 | 11/2002 | Johnson et al. |
| 6,514,265 B2 * | 2/2003 | Ho .............. A61B 17/083 606/157 |
| 6,695,855 B1 | 2/2004 | Gaston |
| 6,740,100 B2 | 5/2004 | Demopulos et al. |
| 6,913,607 B2 | 7/2005 | Ainsworth et al. |
| 6,926,730 B1 | 8/2005 | Nguyen et al. |
| 6,942,668 B2 | 9/2005 | Padget et al. |
| 6,951,561 B2 | 10/2005 | Warren et al. |
| 6,984,241 B2 | 1/2006 | Lubbers et al. |
| 7,008,428 B2 | 3/2006 | Cachia et al. |
| 7,226,468 B2 | 6/2007 | Ruff |
| 7,255,700 B2 | 8/2007 | Kaiser et al. |
| 7,335,215 B2 | 2/2008 | Buckman et al. |
| 7,361,179 B2 | 4/2008 | Rousseau et al. |
| 7,455,683 B2 | 11/2008 | Geissler et al. |
| 7,601,165 B2 | 10/2009 | Stone |
| 7,651,509 B2 | 1/2010 | Bojarski et al. |
| 7,708,759 B2 | 5/2010 | Lubbers et al. |
| 7,846,181 B2 | 12/2010 | Schwartz et al. |
| 7,862,584 B2 | 1/2011 | Lyons et al. |
| 7,959,650 B2 | 6/2011 | Kaiser et al. |
| 8,109,968 B2 | 2/2012 | Ashley et al. |
| 8,439,936 B2 | 5/2013 | McClellan |
| 8,480,692 B2 | 7/2013 | McClellan |
| 2002/0077631 A1 | 6/2002 | Lubbers et al. |
| 2002/0161400 A1 | 10/2002 | Demopulos et al. |
| 2002/0165561 A1 | 11/2002 | Ainsworth et al. |
| 2002/0169359 A1 | 11/2002 | McCarthy et al. |
| 2004/0059357 A1 | 3/2004 | Koseki |
| 2004/0153104 A1 | 8/2004 | Buckman et al. |
| 2004/0186515 A1 | 9/2004 | Rosenblatt |
| 2004/0193217 A1 | 9/2004 | Lubbers et al. |
| 2004/0267309 A1 | 12/2004 | Garvin |
| 2005/0085833 A1 | 4/2005 | Gedebou |
| 2005/0131430 A1 | 6/2005 | Ravikumar |
| 2005/0149122 A1 | 7/2005 | McDevitt et al. |
| 2006/0195103 A1 | 8/2006 | Padget et al. |
| 2006/0276809 A1 | 12/2006 | Oliveira |
| 2007/0021779 A1 | 1/2007 | Garvin et al. |
| 2007/0055258 A1 | 3/2007 | Hansen |
| 2009/0024216 A1 | 1/2009 | Cauthen, III et al. |
| 2009/0221868 A1 | 9/2009 | Evans |
| 2009/0228022 A1 * | 9/2009 | McClellan ......... A61B 17/1146 606/139 |
| 2010/0268273 A1 | 10/2010 | Albertorio |
| 2011/0022050 A1 | 1/2011 | McClellan et al. |
| 2011/0029001 A1 | 2/2011 | Trieu et al. |
| 2012/0046693 A1 | 2/2012 | Denham et al. |
| 2012/0053630 A1 | 3/2012 | Denham et al. |
| 2012/0203253 A1 | 8/2012 | Kubiak |
| 2012/0277770 A1 | 11/2012 | Fenton et al. |
| 2014/0128888 A1 | 5/2014 | McClellan |
| 2014/0257379 A1 | 9/2014 | McClellan |
| 2014/0296887 A1 | 10/2014 | McClellan |

OTHER PUBLICATIONS

Ethicon, "An Exciting New Option for Tissue Control", Stratafix Knotless Tissue Control Device, 2012; 2 Pages.
Covidien, "Reduce Complications with V-Loc Wound Closure Device", http://ep.covidien.com/covidien-vloc-vloc..._source=google&utm_, 2013; 2 pages.
Angiotech, "Quill Redefining Wound Closure", http://www.md.angiotech.com/focus-markets/wound-closure/quill/, 2010; 3 Pages.
Search Report and Written Opinion dated Mar. 21, 2013 for related PCT Application No. PCT/US2012/059705, 9 pages.
Search Report and Written Opinion dated Aug. 21, 2014 for related PCT Application No. PCT/US2014/021712, 8 pages.
Su,Wei-Ren et al., The Modified Finger-Trap Suture Technique: A Biomechanical Comparison of a Novel Suture Technique for Graft Fixation, Jan. 20, 2012, Abstract, 1 page.
Angiotech, "Quill Device", http://www.angiotech.com/focus-markets/wound-closure/guill/, 2011; 3 Pages.
"Ethicon's New STRATAFIX Knotless Tissue Control Devices", http://www.medgadet.com/2012/10/ethicons-new-stratafix-knotless-tissue-control-devices.html/print/, Oct. 5, 2012; 3 Pages.
Covidien, "Announcing...The V-Loc 90 Absorbable Wound Closure Device", http://web.archive.org/web/20100917152329/http://www.covidien.com/vloc/pages.aspx, Sep. 17, 2010; 1 Page.

* cited by examiner

SELF LOCKING KNOTLESS SUTURE

CROSS-REFERENCE TO RELATED APPLICATIONS

The present application claims priority to U.S. Provisional Application No. 61/721,158 filed on Nov. 1, 2012, the contents of which are incorporated herein by reference in their entirety.

BACKGROUND

1. Field of the Invention

The present invention generally relates medical devices and methods for joining tissue, and more particularly to devices and methods for suturing. This invention may be applicable in a manner similar to suture, where various tissues may need to be joined together 2. Discussion of Background Information Surgical suture is commonly used to join various tissues to each other. Suture commonly consists of a needle attached to a length of thread. The suture is passed through the tissues to be joined and a knot is typically tied to secure the final construct.

SUMMARY

Aspects of the invention are directed to self-locking knotless sutures, and associated methods. The sutures and methods described herein may be used for joining tissue. The ability to use a self-locking knotless suture may provide a number of advantages over conventional sutures. A knotless suture may provide the security of a knot while eliminating the bulk of a knot. Additionally, the ease of the procedure does not require the surgeon to learn new techniques. Further, the elimination of knot tying may increase the speed of the procedure potentially decreasing the time the patient is under anesthesia.

In a first aspect of the invention, there is a system for securing tissue including a monofilament and a braid having a fixed end and a capture end. A first end of the monofilament is connected to the fixed end of the braid. A second end of the monofilament opposite the first end is a free end. The capture end of the braid has a first opening and a second opening. The monofilament and braid are structured and arranged for the free end of the monofilament to be inserted into the first opening, passed through a tunnel formed by the braid, and passed out of the second opening, all while moving in a first direction. After insertion of the monofilament into the braid, the braid prevents movement of the monofilament in a second direction opposite the first direction to prevent the monofilament from being pulled out of the braid. In embodiments, the system is a self-locking, knotless suture device.

The braid prevents movement of the monofilament in the second direction opposite the first direction based on a finger trap principle. In particular, when the monofilament moves in the second direction opposite the first direction of insertion, the braid reduces in diameter which, in turn, applies a radial force to the monofilament that prevents the monofilament from pulling out of the braid in the second direction. The braid may be composed of polymer. In some embodiments, the braid is not composed of metal.

In embodiments, fibers of the braid at the capture end are partially embedded in a polymer tube that surrounds the braid. The polymer tube may have a saddle-shape that provides an inward radial force. The fibers of the braid protrude inward to the space of the tunnel formed by the braid.

The system may further include: an introducer wedge connected to the free end of the monofilament; a suture connected to the introducer wedge; and a needle connected to the suture. The system may further include a needle connected to the free end of the monofilament.

The first end of the monofilament may be connected to the fixed end of the braid by melting, welding, or gluing. In additional embodiments, the first end of the monofilament may be connected to the fixed end of the braid by intimate braid or swedging, e.g., one fitting inside the other.

In aspects, the braid is selectively convertible between a first collapsed state and a second open state. A portion of the braid has a first inside diameter in the first collapsed state. The portion of the braid has a second inside diameter in the second collapsed state. The first inside diameter is less than the second inside diameter. An outside diameter of the monofilament is greater than the first inside diameter and less than the second inside diameter.

The braid may be a helically wound, biaxial braid. There may be external protrusions on the monofilament. In additional embodiments, the braid may have a crossed pattern so that some fibers are longitudinal and having crossing fibers that provide stability and strength in a different direction. Further, the braid may be a combination of printed resorbable polymers that form the trap structure.

In embodiments, the first opening of the capture end of the braid is angled such that it is not perpendicular to a central longitudinal axis of the capture end.

In further embodiments, the fixed end of the braid comprises a first fiber mesh tube having a first outside diameter. The capture end of the braid comprises a second fiber mesh tube having a second outside diameter. The first outside diameter is larger than the second outside diameter.

In another aspect of the invention, there is a method of fastening tissue. The method includes fastening tissue using the system that includes the monofilament and the braid. The tissue may comprise a first tissue and a second tissue. The fastening may includes creating a running suture at plural locations in the first tissue and the second tissue.

In another aspect of the invention, there is a method of manufacturing a self locking knotless suture. The method includes manufacturing the system that includes the monofilament and the braid.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
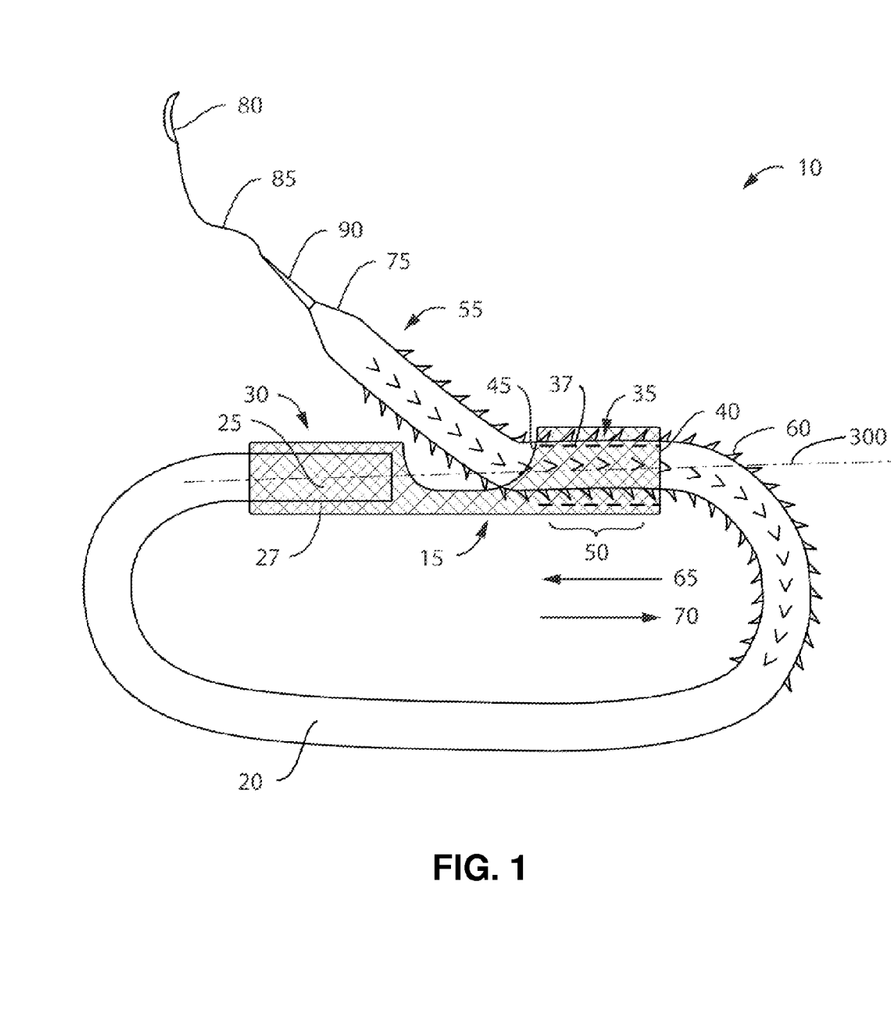
FIG. 1 shows an exemplary self-locking knotless suture in accordance with aspects of the invention.

FIG. 1 shows a combination, self-locking suture 10 comprising both a braided section, e.g., braid 15, and a monofilament section, e.g., monofilament 20, in accordance with aspects of the invention. In embodiments, the monofilament 20 consists of a single strand of a material, while the braid 15 consists of three or more strands of material that are intertwined or woven together. In additional embodiments, a composite structure may be substituted for the monofilament 20, e.g., a second braid with male like features described herein. The braided material of the braid 15 may form a sheath of material strands with a hollow core. The braid material of the braid 15 may be composed of non-resorbable polymers such as polyethylene, polyester, polypropylene or nylon; resorbable polymers such as polyglycolic acid, polylactic acid, or polydioxanone; biological materials such as catgut or silk; metals and any combination thereof.

The braid 15 may be configured such that it can convert between two different states. The braid 15 may change to a "collapsed" configuration as the ends of the braid 15 are pulled apart. This occurs as part of the normal behavior of a helically wound braid whereby the length of the braid 15 increases as the diameter decreases when the ends are pulled away from one another. This occurs as the angles between the adjacent strands decreases at the crossing points, while simultaneously reducing the radial distance across the walls of the braid 15. The braid 15 may also change to an "open" configuration as the two ends of the braid 15 are pushed towards each other, causing the length of the braid 15 to decrease and the diameter to increase.

A section of the monofilament 20 may be connected to a section of the braid 15. One end 25 of the monofilament 20 may be placed inside the hollow core 27 of one end 30 of the braid 15 (e.g., the 'fixed' end 30 of the braid 15, on the left side of FIG. 1) when it is in the "open" configuration. The two sections 25 and 30 may then be joined together by melting, welding, gluing or other bonding techniques. This process forms a single strand of material with a braid 15 on one end and a monofilament 20 on the other end. The diameter of the final construct may be similar to commonly provided surgical suture, which can range from 0.010-0.800 millimeters in diameter. Certain indications may also provide the opportunity for a larger sized strand of material up to several millimeters in diameter to be created. Further, the diameter of the monofilament 20 may be greater than the collapsed diameter of the braid 15, but small enough that it can fit inside the core of the braid 15 when it is in its open configuration diameter.

The opposing end 35 of the braid 15 (e.g., the 'capture' end 35 of the braid 15, on the right side of FIG. 1) may have a passageway or tunnel 37 created in it. The tunnel 37 begins at a first opening 40 in the hollow core at the end 35 of the braid 15 (e.g., the first opening 40 is the right-most opening in FIG. 1), and will end at a second opening 45 some distance from the first opening 40 through the wall of the braid 15 (e.g., the second opening 45 is an opening in the central portion of the braid 15, between the first opening 40 and the end 30 with the monofilament 20). The first opening 40 may be created by fixing a portion of the braid 15 in the "open" configuration, utilizing melting, gluing, welding or other similar operations. This process may help create a smooth entry point for the monofilament 20 while eliminating any fraying that may occur from the ends of the fibers in the braid 15. The second opening 45 may be created by pushing aside the fibers without cutting or disturbing the integrity of any of the fibers of the braid 15. The opening 45 may also then be fixed in this "open" configuration using previously described techniques. Between these two fixed openings 40, 45 is a free section 50 of the braid 15 that can alter between the "open" and "collapsed" configurations as the braid 15 is pushed together or pulled apart, respectively, e.g., in the manner of a finger-trap.

The free end 55 of the monofilament 20 may have a number of directionally biased protrusions 60, or barbs, that extend axially and radially along the length of the free end 55 of the monofilament 20. The directionally biased nature of the protrusions 60 may allow for the monofilament 20 to be inserted into the tunnel 37 of the braid 15 in one direction 65, but engage the braid 15 when it is pulled in the opposing direction 70. The tip 75 of the free end 55 of may also be tapered or angled to facilitate the initial insertion through the tunnel of the braid 15. This tip 75 of the free end may also have a needle 80 or other sharp tipped object that can easily penetrate tissue material.

Once the free end 55 of the monofilament 20 has been passed through the tissue(s) to be joined, the tip 75 of the monofilament is passed through the tunnel 37 of the braid. The resultant loop is shortened by pulling the free end 55 of the monofilament 20 thereby tightening the tissues together. A knot pusher or other instrument may be necessary to facilitate this tightening process. Once the desired level of tension is created in the loop, the remaining free end 55 of the monofilament 20 may be cut off near the braid 15. Since the braid 15 is not directionally biased, the monofilament 20 may be inserted through either the first opening 40 or the second opening 45 of the tunnel 37 in the braid 15. This may help eliminate any confusion or misuse by the user.

The self-locking mechanism may occur as the result of a combination of effects. First, the protrusions 60 on the monofilament 20 may engage the inner walls of the braid 15 to prevent the monofilament 20 from being pulled back out of the braid 15. Second, as the protrusions 60 engage the walls of the braid 15, it may also cause the free section 50 of the tunnel 37 to transform to the collapsed configuration which creates a radial compression on the monofilament 20, i.e., in the manner of a finger trap. These two factors together may create a significantly stronger lock that each individually.

The monofilament 20 may have a number of alternative features on its outer surface that may be used to create the locking mechanism with the braid 15. These features may either be positive or negative in that they may either protrude from or recede into, respectively, the nominal outer diameter of the monofilament 20. Examples of positive features may include bumps, rings, wedges or other extruded shapes of various cross sectional geometries. Element 60 is representative of any such positive features. Examples of negative features may include grooves, slots, troughs, channels or indentations of various cross sectional geometries. Element 60' (in FIG. 3c) is representative of any such negative features. These features 60 and/or 60' may be directionally biased such that the monofilament 20 is able to slide through the braid 15 in one direction 65, but locks when it is pulled in the opposing direction 70.

As described herein, features of devices according to certain aspects of the invention include: a combination monofilament 20 and braid 15 suture; a manner in which the braid 15 is connected to the monofilament 20; the formation of a "tunnel" 37 or "passageway" within the braid 15; and a one-way locking interaction between monofilament 20 and braid 15. Different knotless suture configurations of the device 10 are within the scope of the invention, including but not limited to: a braided catheter tubing construct; a micro-molded trap with monofilament; and a braided suture with tensioning member.

Implementations of the invention may include a method of using the device 10 as described herein. Implementations of the invention may include a method of manufacturing the device 10 as described herein.

Figures 2A, 2B, 2C:
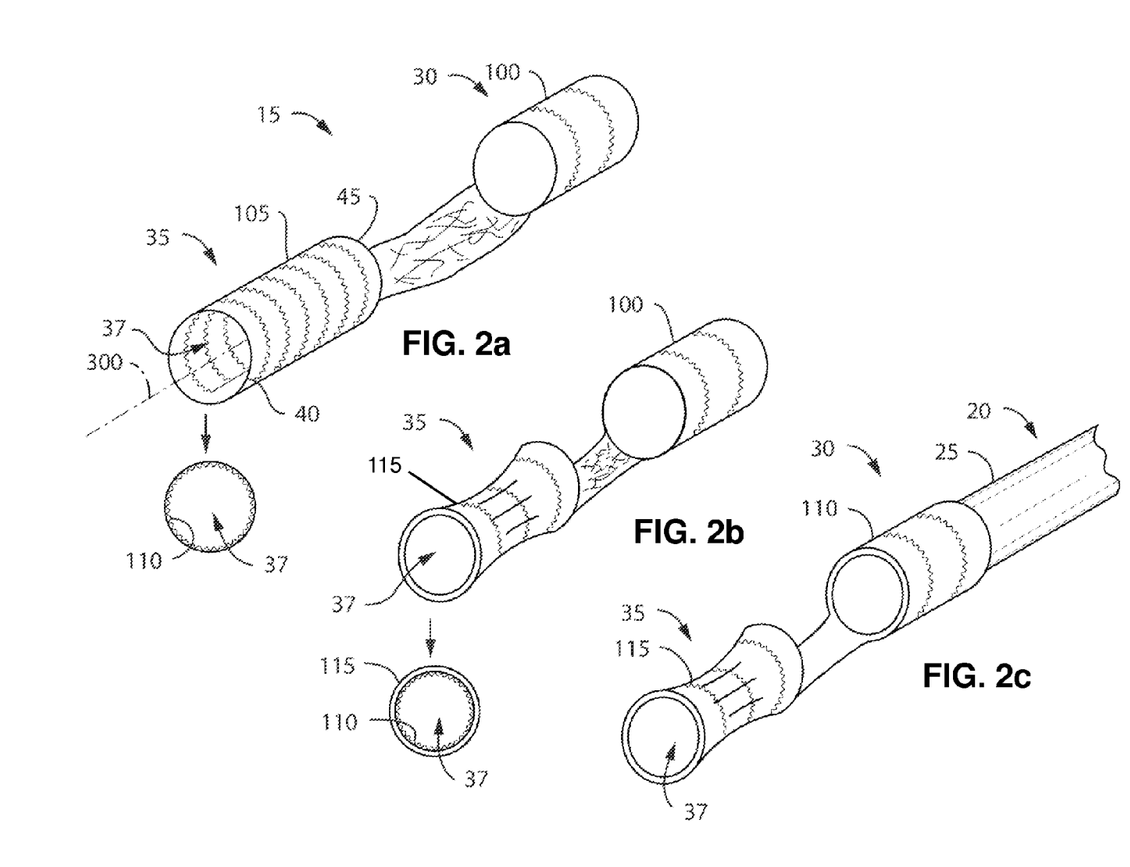
FIGS. 2a-c, 3a-d, 4a-c, and 5a-c show aspects of self-locking knotless sutures in accordance with aspects of the invention.

FIGS. 2*a-c*, 3*a-d*, 4*a-c*, and 5*a-c* show additional or alternative aspects of the device 10 of FIG. 1 in accordance with aspects of the invention. As shown in FIGS. 2*a-c*, the fixed end 30 of the braid 15 may have a larger outside diameter (OD) fiber mesh tube 100 for being bound (e.g., fused) to an end 25 of the monofilament 20, e.g., as specifically shown in FIG. 2*c*. As depicted in FIG. 2*a*, the capture end 35 of the braid 15 may have a braided smaller OD fiber tube 105 into which the other end 55 of the monofilament 20 is inserted and captured during implant in the body, e.g., during suturing.

As depicted in FIG. 2*b*, a tube 115 may be shaped to provide an inward radial force, and may be for example injection molded around the fibers 110 of the braid 15. In embodiments, fibers 110 that make up the braid 15 at the capture end 35 of the braid 15 may be partially embedded (e.g., about ½) in the plastic tube 115 that surrounds the braided tube 105. The fibers 110 thus embedded may protrude into the interior space of the tunnel 37 formed by the braid 15. The protrusion of the fibers 110 into the space of the tunnel 37 accelerates the start of the finger-trap based gripping when the monofilament 20 begins to pull out of the braided capture tube of the braid 15. The tube 115 may be a plastic material that is shaped to provide an inward radial force.

As depicted in FIG. 2*c*, the monofilament 20 may have three dimensional knurling that functions like hooks to interact with the interior of the larger OD tube 100 at the end 25 of the braid 15. In this manner, the larger OD fiber tube 100 is bound to the monofilament 20 creating one structure. Because of the interaction between the knurled monofilament 20 and the fibers of the braid 15, the radial force of the braid 15 on the monofilament 20 to hold the monofilament 20 in the braid 15 is less than a system without such knurling, which provides more latitude in selecting materials of construction for the device (e.g., the braid may be formed of plastic or resorbable polymer).

Figures 3A, 3B, 3C, 3D:
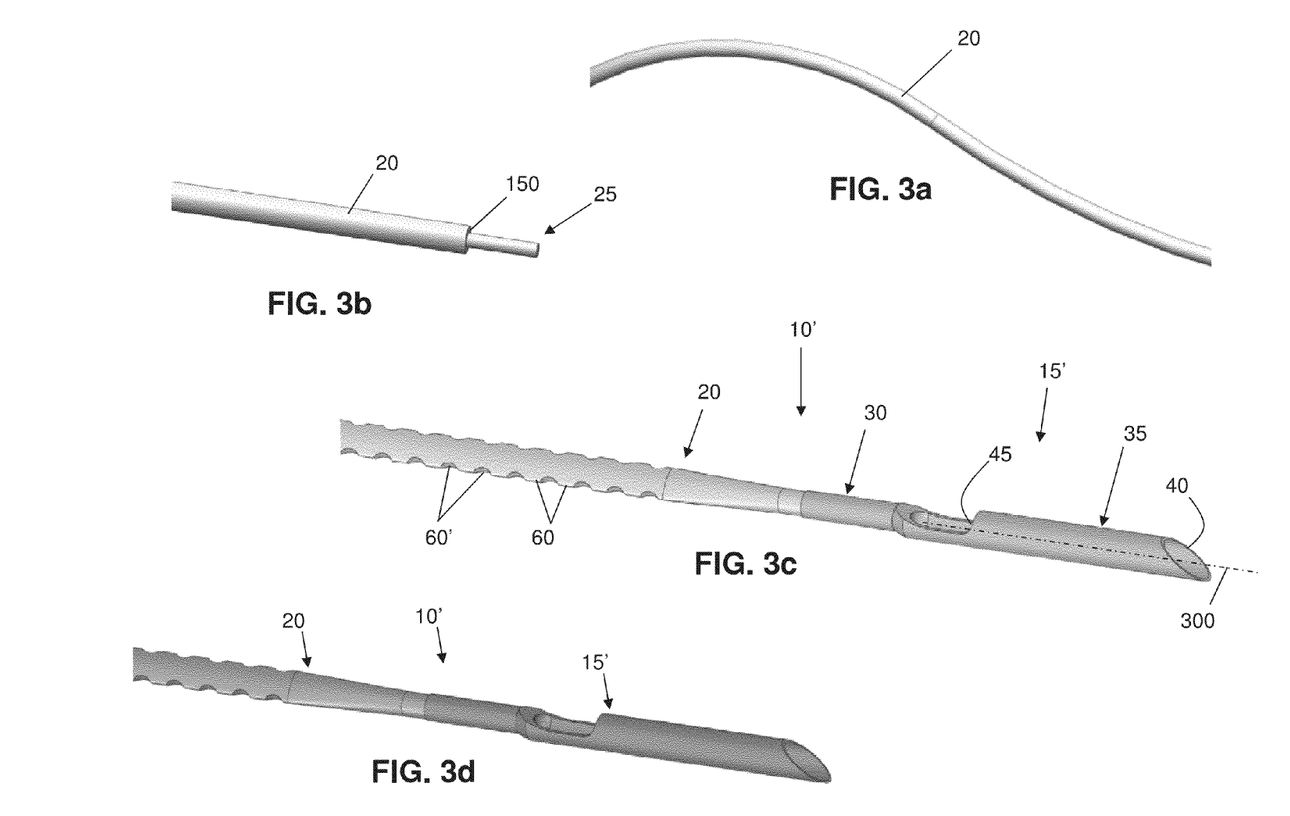

FIGS. 3*a-d* show an exemplary process for making a micro-molded trap device 10' and in particular of bonding the monofilament 20 to the fixed end 30 of the braid 15' in accordance with aspects of the invention. FIG. 3*a* shows the monofilament 20 as an extruded nylon monofilament. FIG. 3*b* shows creating a shoulder 150 at the end 25 of the monofilament 20. The shoulder 150 may be formed in any suitable manner, such as using an Excimer laser. FIG. 3*c* shows overmolding the nylon trap (i.e., braid 15') onto the end 25 of the monofilament 20. FIG. 3*c* also shows features 60, 60' (e.g., shapes) formed along the length of the monofilament 20. The features 60 and/or 60' may be thermally formed during the molding process, for example, although any suitable forming may be used within the scope of the invention. FIG. 3*d* depicts irradiating the device 10' to cros slink polymer chains and significantly increase strength. Implementations of the invention may include a method of manufacturing the device 10' as described herein.

Figures 4A, 4B:
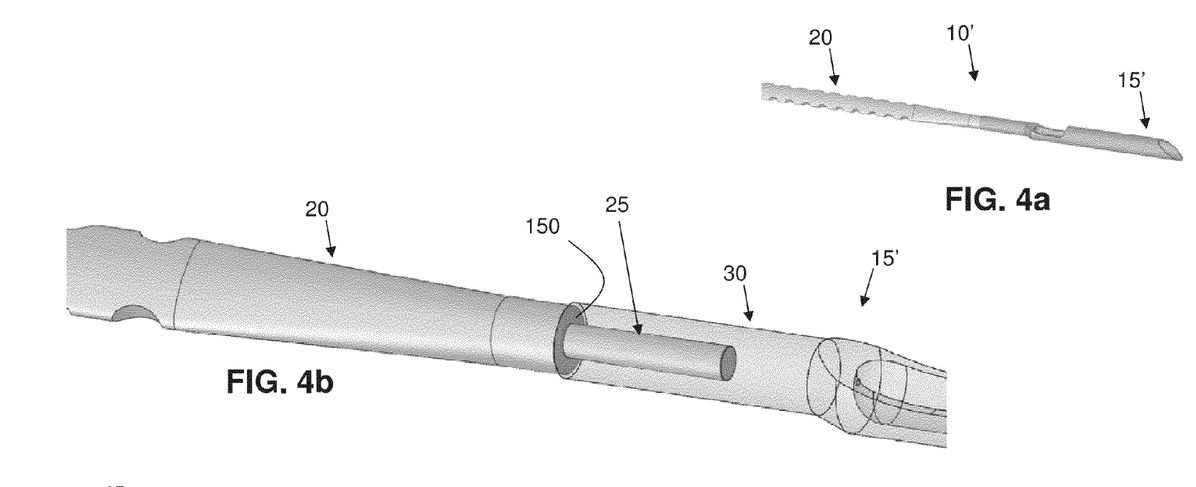
Figure 4C:
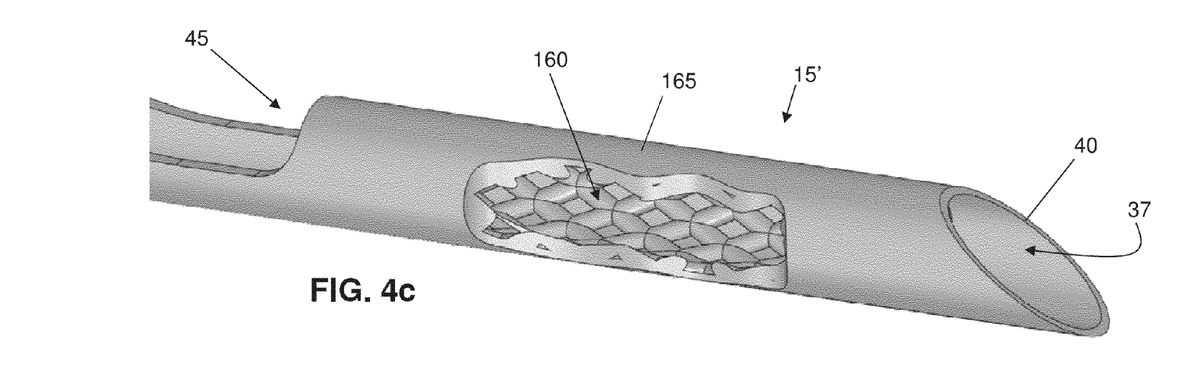

FIGS. 4*a-c* show an exemplary internal structure of the micro-molded trap device 10', in particular of the capture end 35 of the braided element (e.g., braid 15') in accordance with aspects of the invention. In an embodiment of device 10' the braid 15' comprises a finger trap that is molded with internal lattice features 160 that function in s similar manner as braid 15 of FIG. 1 to capture the monofilament 20 based on the finger trap principle. As shown in FIG. 4*b*, end 30 of the trap element (e.g., braid 15') is overmolded onto the end 25 of the monofilament 20 at the shoulder 150, thus providing a structural attachment. As shown in FIG. 4*c*, the trap element (e.g., braid 15') is molded with internal lattice features 160 and a thin over-skin 165 that allows the trap element to flex and receive the oval-shaped monofilament 20. The molded trap element (e.g., braid 15') may be formed using a sacrificial core pin to create the internal lattice features 160, the core pin being disintegrated (e.g., crumbled by irradiation) after forming the lattice features 160.

Figures 5A, 5B, 5C:
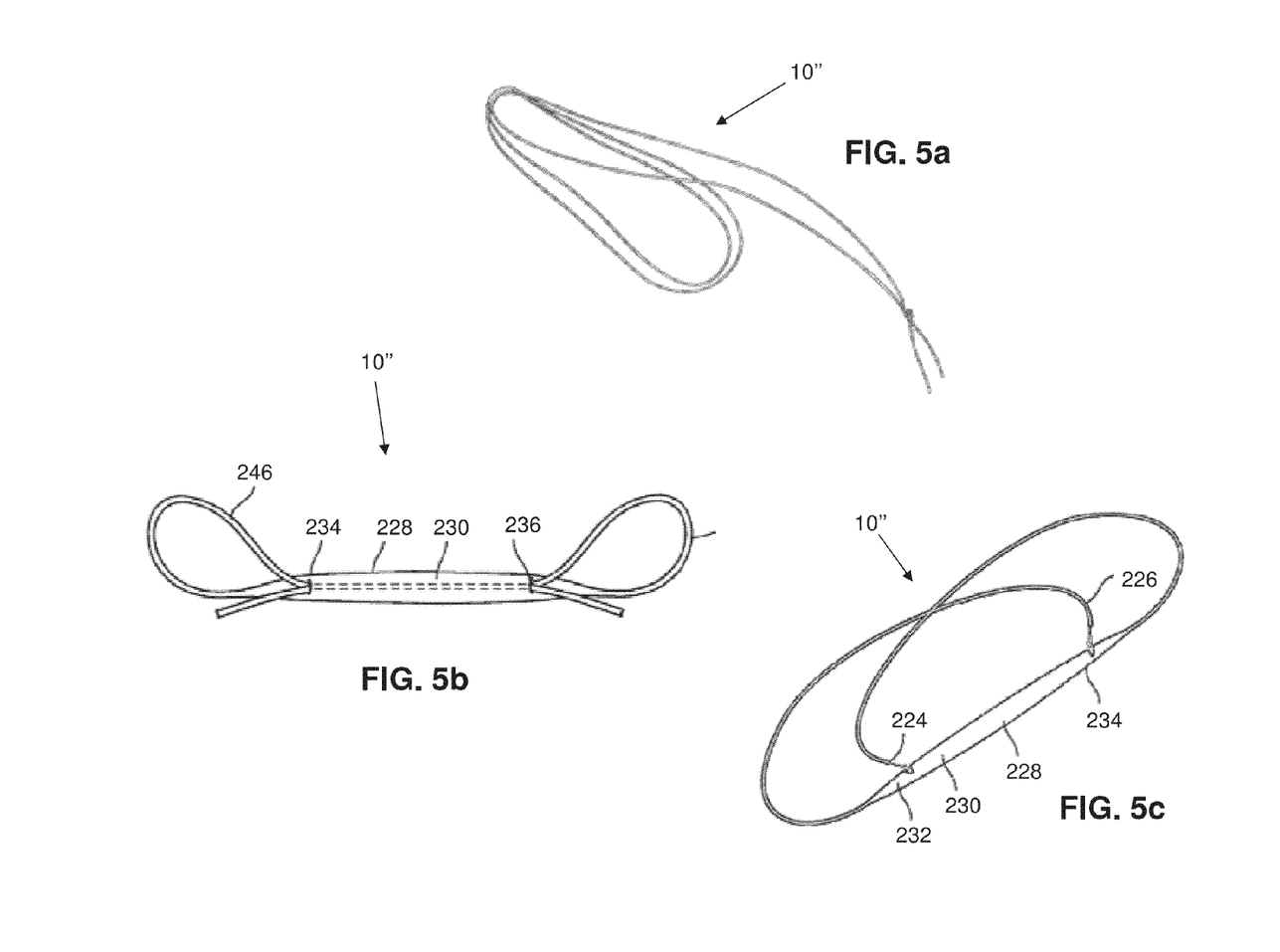

FIGS. 5*a-c* show an exemplary embodiment of a braided suture with tensioning member 10" in accordance with aspects of the invention. This device 10" includes an interwoven suture 246 with an attached tensioning member 228. Ends 224, 226 of the suture 246 may be inserted into a tunnel 230 of the tensioning member 228 at respective openings 234, 236 of the tensioning member 228.

Referring again to FIGS. 1 and 2*a-c*, according to aspects of the invention, the capture end 35 of the braid 15 comprises a tubular braid that operates in the manner of a finger trap to lock the insertion end (e.g., free end 55) of the monofilament 20 to the braid 15 when the free end 55 of the monofilament 20 is located inside the braid 15. In some embodiments, the braid 15 is a helically wound braid, e.g., a biaxial braid. Applying opposing forces to the braid 15 along its longitudinal axis 300 outward from the center of the braid 15 increases the length of the braid 15 while also decreasing the circumference of the braid 15. The length of the braid 15 is increased by reducing the angle between the crossing fibers at their crossing points, which simultaneously reduces the radial distance from the axis to the fibers, which decreases the circumference of the braid 15, which in turn increases the gripping force on the end of the monofilament 20 inside the braid (according to the finger trap principle) to prevent the monofilament 20 from being pulled out of the braid 15. The more the braid 15 is lengthened along the axis 300, the more the circumference shrinks (i.e. the trap tightens).

When the monofilament 20 is fixed/fused/bound to the fixed end 30 of the braid 15, the device 10 takes the form of a single elongate element having a male end (the free end 55 of the monofilament that is not fused in the braid 15) and a female end (the capture end 35 of the braid 15). The free end 55 of the monofilament may optionally be provided with a needle 80 and/or suture 85 and/or introducer wedge 90 to assist in passing the monofilament 20 through tissue.

In accordance with aspects of the invention, the knotless suture system (e.g., device 10) is structured and arranged such that the insertion end 55 of the monofilament 20 enters the capture tube (e.g., capture end 35) of the braid 15 at the first opening 40, passes through the braided capture element (e.g., capture end 35) moving in a first direction 65 (i.e., from the first opening 40 toward the second opening 45), and exits the capture tube at the second opening 45. Utilizing the finger-trap principle, the capture element securely engages the monofilament 20 and prevents the monofilament 20 from backing out of the capture tube, i.e., prevents movement of the monofilament 20 relative to the capture tube in a second direction 70 opposite the first direction 65.

In embodiments, the first opening 40 of the capture end 35 of the braid 15 is provided by an angled cut of the hollow body, i.e., in a plane that is not perpendicular to a central longitudinal axis 300 of the hollow body. The angled cut facilitates locating the first opening 40 with the free end 55 of the monofilament 20 when first inserting the free end 55 of the monofilament 20 into the first opening 40. The angled cut also facilitates pushing the capture tube into the tissue during completion of the suture.

In an exemplary operation of the knotless suture system in accordance with aspects of the invention, the needle 80 and monofilament 20 may be used to create a running suture at plural locations in a first tissue and a second tissue, which may be portions of a cut tendon, for example. After completion of the plural sutures, the needle 80 is inserted into the first opening 40 of the capture end 35 of the braid 15, passed through the capture element, and moved out of the capture tube through the second opening 45. The needle 80 and/or monofilament 20 are then used to pull a portion of the remaining monofilament 20 through the capture tube, which causes the first tissue and second tissue to move toward one another. When the first tissue and second tissue are sufficiently approximated, the excess portion of the monofilament 20 is cut at just outside the second opening 45. According to aspects of the invention, the capture element prevents the monofilament 20 from backing out of the capture tube, such that a secure running suture is provided without having to tie any knots. After approximating the tissue, the capture tube may be left outside the tissue or may pushed through the sidewall of the tissue and housed within the tissue. For example, a knot pusher tool may be used to advance the capture tube through a tendon sidewall and into the inner portion of the tendon. Further, the method is not limited to that described above, and variations may be employed. For example, the needle itself, or the loose end after the needle has been cut off, can be passed through the first opening and out of the second opening. Alternatively, the needle may be left on the free end, passed part-way through the braided trap via the first opening, and passed through the sidewall of the braided trap without passing through the second opening.

It is noted that the invention is not limited to the exemplary use described above. For example, the knotless suture system may be used to secure other types of tissue, and is not limited to use with two portions of a tendon. Also, different types of running sutures may be provided, or alternatively the system can be used to provide a single suture between two tissues. Additionally, the monofilament may be advanced through the capture tube by holding the monofilament still and pushing the capture tube along the insertion element monofilament, or by a combination of pulling the monofilament and pushing the capture tube. Moreover, the needle, needle and suture, or needle and suture and wedge may be removed (e.g., cut off from the remainder of the monofilament) prior to passing the monofilament through the capture tube.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A system for securing tissue, comprising: a monofilament; and a braid having a fixed end and a capture end; wherein: a first end of the monofilament is connected to the fixed end of the braid; a second end of the monofilament opposite the first end is a free end; the capture end of the braid has a first opening and a second opening; the monofilament and braid are structured and arranged for the free end of the monofilament to be inserted into the first opening, passed through a tunnel formed by the braid, and passed out of the second opening all while moving in a first direction; and after insertion of the monofilament into the braid, the braid prevents movement of the monofilament in a second direction opposite the first direction to prevent the monofilament from being pulled out of the braid, wherein: the fixed end of the braid comprises a first fiber mesh tube having a first outside diameter; the capture end of the braid comprises a second fiber mesh tube having a second outside diameter; and the first outside diameter is lamer than the second outside diameter.

2. The system of claim 1, wherein the braid prevents movement of the monofilament in the second direction opposite the first direction based on a finger trap principle.

3. The system of claim 1, wherein the braid is composed of polymer.

4. The system of claim 1, wherein fibers of the braid at the capture end are partially embedded in a polymer tube that surrounds the braid.

5. The system of claim 4, wherein the fibers of the braid protrude inward to the space of the tunnel formed by the braid.

6. The system of claim 1, further comprising:
   an introducer wedge connected to the free end of the monofilament;
   a suture connected to the introducer wedge; and
   a needle connected to the suture.

7. The system of claim 1, further comprising a needle connected to the free end of the monofilament.

8. The system of claim 1, wherein the first end of the monofilament is connected to the fixed end of the braid by melting, welding, or gluing.

9. The system of claim 1, wherein the braid is not composed of metal.

10. The system of claim 1, wherein the braid is selectively convertible between a first collapsed state and a second open state.

11. The system of claim 1, wherein the braid is a helically wound, biaxial braid.

12. The system of claim 1, further comprising external protrusions on the monofilament.

13. The system of claim 1, wherein the first opening of the capture end of the braid is angled such that it is not perpendicular to a central longitudinal axis of the capture end.

14. A method of fastening tissue, comprising:
   fastening tissue using the system of claim 1.

15. The method of claim 14, wherein the tissue comprises a first tissue and a second tissue.

16. The method of claim 15, wherein the fastening includes creating a running suture at plural locations in the first tissue and the second tissue.

* * * * *